United States Patent [19]

Hauck

[11] Patent Number: 4,747,837

[45] Date of Patent: May 31, 1988

[54] SYRINGE NEEDLE RECAPPING PROTECTIVE DEVICE

[76] Inventor: Martin W. Hauck, 45 S. Lake Dr., Hillsboro, Mo. 63050

[21] Appl. No.: 44,576

[22] Filed: May 1, 1987

[51] Int. Cl.$^4$ ............................................. A61M 5/32
[52] U.S. Cl. ..................................... 604/198; 604/263
[58] Field of Search ............... 604/198, 192, 263, 187, 604/197

[56] References Cited

U.S. PATENT DOCUMENTS 4,373,526  2/1983  Kling ..................................... 604/198
4,631,057  12/1986  Mitchell ............................... 604/198

Primary Examiner—John D. Yasko
Attorney, Agent, or Firm—Richard L. Miller

[57] ABSTRACT

This device is designed to cover and prevent a hypodermic needle in a syringe from possibly scratching a person after it has been used and discarded, which will help prevent spread of contagious diseases. Primarily, it consists of a transparent sleeve that receives the barrel of a hypodermic syringe, and after the needle has been used, the sleeve is pushed forward to cover the needle. The sleeve and the barrel of the syringe cooperate with each other to lock in the forward and needle covering position, by having a self-contained locking mechanism.

5 Claims, 1 Drawing Sheet

SYRINGE NEEDLE RECAPPING PROTECTIVE DEVICE

BACKGROUND OF THE INVENTION

The instant invention relates generally to hypodermic syringes, and more particularly, to a syringe needle recapping protective device.

Numerous hypodermic devices have been provided in the prior art that are adapted to provide greater safety against contamination. For example, U.S. Pat. Nos. 3,825,003 to Kruck; 3,820,652, to Thackston; and 3,381,813 to Coanda et al all are illustrative of such prior art. While these units may be suitable for the particular purpose to which they address, they would not be as suitable for the purpose of the present invention as hereafter described.

SUMMARY OF THE INVENTION

A primary object of the present invention is to provide a syringe needle recapping protective that will overcome the shortcomings of the prior art devices.

Another object is to provide a syringe needle recapping protective device, which will be of such design, as to include a plastic protective sleeve that will encase a standard hypodermic needle.

Presently the health care professions are using disposable syringes for drug injectables. These syringes are designed for simple use and they are to be thrown away after wards. They come equipped with sterile needles detached until use. The needle has a plastic shield fitting over it and is removed prior to filling and injection. After use the syringes are to be discarded with needle intact. Syringes are discarded by dropping into designated containers carried to the injection site or returned to designated disposal area.

Government facilities as well as the private sector now are promoting safety measures concerning the recapping of disposable syringes. Past measures used the protective sheath needles came with to ensure safety following injections. The reason recapping of needles with the protective sheath in which they are supplied is to be prevented, is because there is a possibility of a technician, nurse, doctor or other person administering an injection of accidentally sticking ones self with the used and thus contaminated needle. This has become of greater importance since diseases such as AIDS has increased the risk to persons administering drugs via syringes.

The present system used requires carrying bulky containers to the bedside or carrying the used syringe back to disposal area. This system leaves much be desired. While effective in certain areas where conditions are not limited by adverse factors, many circumstances still lead to the recapping of needles.

An additional object is to provide a syringe needle recapping protective device, which will have a locking mechanism for retaining it on the barrel of a syringe.

A further object is to provide syringe needle recapping protective device that is simple and easy to use.

A still further object is to provide a syringe needle recapping protective device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows.

DETAILED DESCRIPTION OF THE PREFERRED EMBODIMENTS

Figure 1:
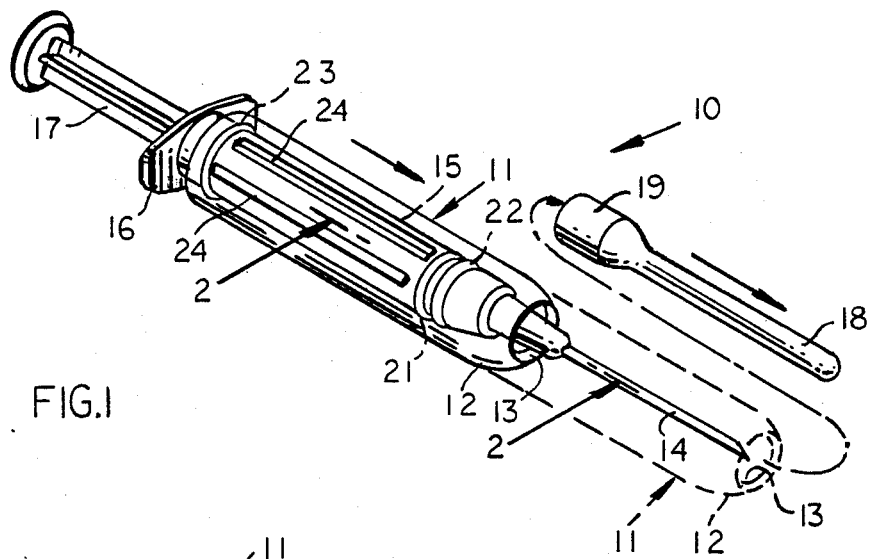
FIG. 1 is a perspective view of the invention incorporated with an other wise conventional hypodermic syringe.

Turning now descriptively to the drawings, in which like reference characters denote like elements throughout the several views, FIG. 1 illustrates a hypodermic syringe 10 that includes a cylindrical sheath sleeve 11 which may be formed of a clear plastic having a rounded forward end 12 with an opening 13 for freely receiving a standard gauge needle 14 received on the forward end of barrel 15. When retracted, the larger rear open end of sleeve 11 is adjacent to the finger grip portion 16 of barrel 15, from which the plunger projects. A sterile needle cap 18 is provided on needle 14 of the assembly, and its base 19 is also received in the opening 13 of sleeve 11. A locking mechanism 20 is provided, so as to retain sleeve 11 on the barrel 15 when sleeve 11 is in its full forward position for encasing needle 14, and mechanism 20 consist of a pair of annular and spaced-apart flanges 21 and 22. Flanges 21 and 22 are integrally attached and project from the outer periphery of the barrel 11, and flange 21 is chamfered for sliding engagement with a similarly chamfered inner annular flange 23 that is integrally attached to sleeve 11. When sleeve 11 is fully advanced forward to cover the exposed needle 14, the chamfered flange 23 cam rides over the chamfered flange 21 and disposes itself between flanges 21 and 22, thus locking sleeve 11 in its advanced position which encases needle 14 so as to prevent a person from possibly being accidently contaminated with the used needle 14 when the syringe 10 is discarded.

It shall also be noted, that longitudinal and radially spaced openings 24 are provided through sleeve 11, enabling greater visibility of the locking mechanism 20 and providing the necessary flexibility of sleeve 11, for the locking and retaining to take place when inner flange 23 moves between the spaced flanges 21 and 22 of barrel 15.

In use, sleeve 11 is gripped in one's fingers and pushed forward to its locked condition, which completely covers the needle 14 to prevent needle 14 from accidently scratching anyone after it has been used. The above locked condition occurs when inner flange 23 is disposed between the pair of outer flanges 21 and 22 of the barrel 15.

Figure 3:
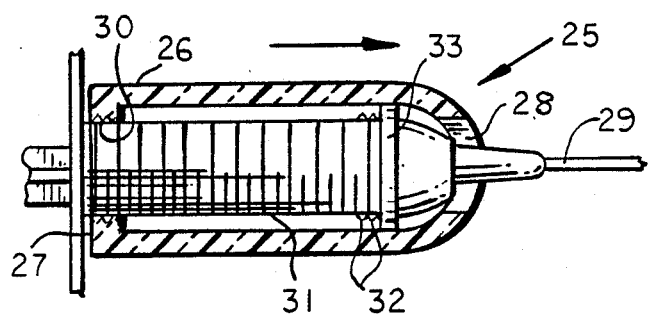
FIG. 3 is a cross sectional view of a modification showing an alternate thread locking mechanism.

Referring now to FIG. 3 of the drawing, a modified syringe 25 is shown to include a clear plastic sleeve 26 having a rear end wall 27 integrally attached. An opening 28 is provided in the front of sleeve 26 for the projection of needle 29 when it is to be used, and a threaded opening 30 is provided through end wall 27, for freely receiving the barrel 31. When sleeve 26 if brought forward to cover needle 29 after its use, sleeve 26 is retained on barrel 31 by the threads 32 of the barrel 26 engaging with the threaded opening 30 through end wall 27. An annular flange 33 is integrally attached to the front portion of barrel 31, and serves as a stop against further forward travel of the barrel 26 after it has covered the needle 29.

In use, sleeve 26 functions in the same manner as that described for barrel 15 of syringe 10, with the exception, that locking of the sleeve 26 is effected by rotating sleeve 26 at its forward position, until the the threads 32 fully engage with those of the end wall 27.

Figure 2:
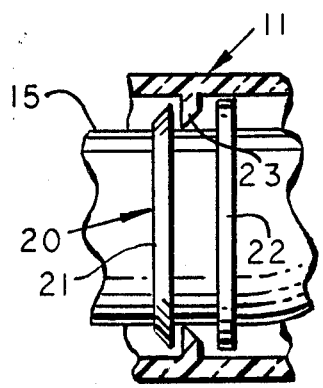
FIG. 2 is an enlarged fragmentary cross sectional view taken on line 2—2 in FIG. 1 showing the locking mechanism therein.
Figure 4:
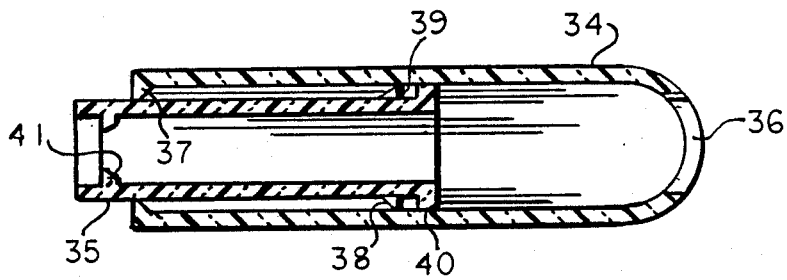
FIG. 4 is a cross sectional view of a still further modification having a telescopic sheath.

Looking now at FIG. 4, another modified form of outer sleeve 34 includes a smaller and telescoping inner sleeve 35, and this structure is designed to be employed where needle lengths surpass syringe length. A front opening 36 is provided in sleeve 34, for freely receiving a needle (not shown), and an annular inner flange 37 is in integrally attached to the opposite end of sleeve 34, for riding up and over a similar shaped flange 38 integrally attached and extending from the outer periphery of inner sleeve 35. When sleeve 34 is fully extended to cover a needle, flange 37 is designed to lodge in the annular groove 39 provided between flange 38 and end flange 40 of inner sleeve 35. A third and inner annular chamfered flange 41 is integrally attached to inner sleeve 35, and serves to retain inner sleeve 35 on the barrel 15 in a similar manner heretofore described on FIGS. 1 and 2, which has the pair of flanges 21 and 22 for locking purposes.

In use, the telescoping sleeves 34 and 35 function to encase protectively, needle lengths that surpass syringe length. When sleeve 34 is pulled fully forward to effect same, the flange 37 thereof, engages within the annular groove 39.

It is to be additionally noted that when the sleeve is being moved into the protective position the direction that the user's hand would slip (shown by the arrow in FIG. 3) should his/her grasp be accidentally lost would be away from the contaminated needle point and so that no possibility of sticking ones self is at all present. This is exactly opposite of what occurs when using the protective sheath supplied with most needles for recapping and the user accidental mis-aligns the sheath when recapping a needle and sticks himself/herself.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A syringe needle recapping protective device, comprising, a sleeve, for being drawn over and covering a hypodermic needle, a syringe received in a said sleeve having a barrel with a forward end retaining said hypodermic needle and a rearward end supporting a plunger, and locking means secured to said sleeve and said barrel of said syringe, wherein said sleeve includes a rear opening and a front opening and is freely slideable on said barrel of said syringe until locked in extended position covering said needle, and said locking means limits further travel of said sleeve after said sleeve covers said needle, and comprises an inner directed annular flange integrally attached to said sleeve and a pair of spaced outer directed flanges integrally attached to said barrel, and wherein a forward one of said pair of spaced outer directed flanges of said barrel is chamfered to engage and cam against a similarly chamfered peripheral edge of said inner directed annular flange of said sleeve, causing said inner directed annular flange of said sleeve to lodge between said spaced outer directed flanges and lock said sleeve in the extended position covering said needle, a rearward one of said pair of spaced outer directed flanges of said barrel having an outer diameter greater than a diameter of the inner directed annular flange, the inner directed annular flange having a rearward directed face radially inwardly of the periphery of the rearward flange, whereby the inner directed annular flange is locked in place and the sleeve cannot be removed rearwardly from its position covering the needle.

2. A syringe needle recapping protective device as set forth in claim 1, wherein said sleeve includes a rear opening and a front opening and is freely slidable on said barrel of said syringe until locked in extended position covering said needle, and said locking means limits further travel of said sleeve after said sleeve covers said needle, and comprises an inner and annular flange integrally attached to said sleeve and a pair of spaced and outer flanges integrally attached to said barrel.

3. A syringe needle recapping protective device as set forth in claim 2, wherein one of said pair of spaced and outer flanges of said barrel is chamfered to engage and cam against a similarly chamfered edge of said inner and annular flange of said sleeve, causing said inner and annular flange of said sleeve to lodge between said spaced and outer flanges and lock said sleeve in forward position covering said needle.

4. A syringe needle recapping protective device as set forth in claim 1, wherein a plurality of longitudinal openings are spaced from each other through said sleeve and causes necessary flexibility of said sleeve and visual observation of the locking of said sleeve in said forward position covering said needle.

5. A syringe needle recapping protective device as set forth in claim 4, wherein a base portion of a needle cap on said needle is freely received in the front opening provided in said sleeve when said sleeve is in full retracted position on said barrel.

* * * * *